(12) United States Patent
Heydt et al.

(10) Patent No.: US 12,297,174 B2
(45) Date of Patent: May 13, 2025

(54) HETEROGENEOUS CATALYZED PROCESS FOR THE PRODUCTION OF 2,2,6,6-TETRAMETHYL-4-PIPERIDONE

(71) Applicant: BASF SE, Ludwigshafen am Rhein (DE)

(72) Inventors: Thomas Heydt, Ludwigshafen (DE); Michael Schmitt, Ludwigshafen (DE); Alvaro Gordillo Bolonio, Ludwigshafen (DE); Andrei-Nicolae Parvulescu, Ludwigshafen (DE); Ulrich Mueller, Ludwigshafen (DE); Michael Kuebler, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 650 days.

(21) Appl. No.: 17/613,677

(22) PCT Filed: May 24, 2020

(86) PCT No.: PCT/EP2020/064351
§ 371 (c)(1),
(2) Date: Nov. 23, 2021

(87) PCT Pub. No.: WO2020/239651
PCT Pub. Date: Dec. 3, 2020

(65) Prior Publication Data
US 2022/0227710 A1  Jul. 21, 2022

(30) Foreign Application Priority Data
May 24, 2019 (EP) ..................... 19176452

(51) Int. Cl.
*C07D 211/74* (2006.01)
(52) U.S. Cl.
CPC ................. *C07D 211/74* (2013.01)
(58) Field of Classification Search
CPC .................................................. C07D 211/74
See application file for complete search history.

(56) References Cited

U.S. PATENT DOCUMENTS

| 5,316,993 | A | 5/1994 | Sextl et al. | |
| 6,646,127 | B2 * | 11/2003 | Malz, Jr. .............. | C07D 211/74 502/263 |
| 2010/0305146 | A1 | 12/2010 | Brandenburg et al. | |

FOREIGN PATENT DOCUMENTS

| CN | 107033066 A | 8/2017 |
| CN | 107915673 A | 4/2018 |
| EP | 0004104 A2 | 9/1979 |
| EP | 0516949 B1 | 8/1994 |
| JP | 2003-252858 A | 9/2003 |
| JP | 2014-058515 A | 4/2014 |
| JP | 2017-202951 A | 11/2017 |
| JP | 2017-210399 A | 11/2017 |
| JP | 2018-087105 A | 6/2018 |
| KR | 10-1996-0000018 B1 | 1/1996 |

OTHER PUBLICATIONS

Gliozzi et al., 393 J. of Mol. Catalysis A: Chemical, 325-332 (2014) (Year: 2014).*
European Search Report for EP Patent Application No. 19176452.1, Issued on Oct. 28, 2019, 3 pages.
Gliozzi, et al., "Towards a more sustainable production of triacetoneamine with heterogeneous catalysis", Journal of Molecular Catalysis A: Chemical, vol. 393, Nov. 1, 2014, pp. 325-332.
Harris, et al., "Further conventions for NMR shielding and chemical shifts (IUPAC Recommendations 2008)", Pure and Applied Chemistry, vol. 80, Issue 1, 2008, pp. 59-84.
International Search Report for PCT Patent Application No. PCT/EP2020/064351, Issued on Jul. 22, 2020, 4 pages.
Tian, et al., "Effect of Alkali Treatment of HY Zeolite on Continuous Synthesis of Triacetonamine", Journal of Heterocyclic Chemistry, vol. 52, Issue 5, Jul. 31, 2004, pp. 1377-1381.

* cited by examiner

*Primary Examiner* — Timothy R Rozof
(74) *Attorney, Agent, or Firm* — ArentFox Schiff LLP (57) ABSTRACT

The present invention relates to a process for the production of 2,2,6,6-tetramethyl-4-piperidone particularly comprising
(i) providing a reactor containing a catalyst comprising a zeolitic material having a framework structure of FAU, wherein the zeolitic material comprises $YO_2$ and $X_2O_3$ in its framework structure, wherein Y is a tetravalent element and X is a trivalent element, wherein the zeolitic material has an $YO_2$ to $X_2O_3$ molar ratio of 16 to 175;
(ii) preparing a reaction mixture comprising acetone and ammonia;
(iii) contacting the catalyst in the reactor with the reaction mixture prepared in (ii) at a temperature in the range of from 40 to 250° C. for obtaining a reaction product comprising 2,2,6,6-tetramethyl-4-piperidone;
wherein the mixture prepared in (ii) and contacted with the catalyst in (iii) contains less than 10 weight-% of water based on 100 weight-% of the reaction mixture.

13 Claims, 1 Drawing Sheet

HETEROGENEOUS CATALYZED PROCESS FOR THE PRODUCTION OF 2,2,6,6-TETRAMETHYL-4-PIPERIDONE

CROSS-REFERENCE TO RELATED APPLICATIONS

This application is a National Stage Entry of PCT/EP2020/064351, filed May 24, 2020, which claims priority to EP Application Serial No. 19176452.1, filed May 24, 2019, the disclosures of each of which are hereby incorporated by reference in their entirety.

TECHNICAL FIELD

The present invention relates to a process for the production of 2,2,6,6-tetramethyl-4-piperidone.

INTRODUCTION 2,2,6,6-tetramethyl-4-piperidone is used as a key intermediate in industrial organic chemistry. The preparation of 2,2,6,6-tetramethyl-4-piperidone usually proceeds via a complex system of equilibria in a continuous or semi-continuous process in which acetone is converted with ammonia in the presence of a catalyst. Typically, ammonium salts are used as homogeneous catalyst. The type of the conversion may be classified as cyclocondensation reaction, whereby water is set free. The work-up procedure is usually done by extraction with caustic soda to remove water and to neutralize the catalyst. After that, acetone remainders are separated from the organic phase which is subsequently fractionated.

Cavani et al. discloses a study on the acid-catalyzed condensation of acetone and ammonia to directly produce 2,2,6,6-tetramethyl-4-piperidineone under both homogeneous and heterogeneous conditions, wherein aqueous ammonia is used as the ammonia source. As catalysts, H-Y zeolites have been tested having selected features. It has been found that by-products are formed during the preparation of 2,2,6,6-tetramethyl-4-piperidone. Said by-products may contain diacetonealcohol, diacetoneamine, mesityl oxide, 1,2,5,6-tetrahydro-2,2,4,6,6-pentamethylpyrimidine, and 2,2,4,6-tetramethyl-2,3-dihydropyridine, wherein the latter is the most undesired by-product since its formation was found to be irreversible. According to Cavani et al. 1,2,5,6-tetrahydro-2,2,4,6,6-pentamethyl-pyrimidine may transform into 2,2,6,6-tetramethyl-4-piperidone either with the insertion of water and elimination of ammonia or, in the presence of acetone, with acetone, with acetone insertion and elimination of 2-iminopropane. Further, it was found that for H-Y zeolites having different silica to alumina ratios (SAR=6; 15; 200) the selectivity towards 2,2,6,6-tetramethyl-4-piperidone increased the lower the SAR was, whereas the selectivity towards undesired 2,2,4,6-tetramethyl-2,3-dihydropyridine was the highest for the H-Y zeolite having a SAR of 15 and the lowest for the H-Y zeolite having a SAR of 6.

CN 107033066 A particularly relates to a method and a special device for the heterogeneous catalyzed synthesis of 2,2,6,6-tetramethyl-4-piperidone. As a heterogeneous catalyst, a Lewis acid catalyst insoluble in water and acetone may be used, including an ion exchange resin, a molecular sieve type catalyst, a (doped) metal oxide, a (doped) metal hydroxide, or a composite of one or more of solid organic sulfonic acid, solid organic carboxylic acid, supported metal halide, supported organic ammonium salt, or solid super acid. In example 1, an organic sulfonic acid-modified exchange resin was used, in example 2 a ferric chloride-supporting molecular sieve, in example 3 a nano-alumina modified catalyst, in example 4 a nano-alumina modified catalyst and organic sulfonic acid-modified ion exchange resin, and in example 5 a nano-alumina modified catalyst and a molecular sieve catalyst supporting ferric chloride. The method comprises using a heterogeneous catalyst, reacting acetone with ammonia gas in a reaction kettle at 60-75° C. for 7 hours, whereby a water separator is used to separate water from the reaction mixture. After work-up, the crude 2,2,6,6-tetramethyl-4-piperidone is purified by rectification. An ion exchange resin or a molecular sieve may be used as Lewis acid catalyst in the disclosed method.

J. Tian et al. disclose a study on the effect of HY zeolite on a continuous synthesis of 2,2,6,6-tetramethyl-4-piperidone, wherein also HZSM-5 and H beta zeolites were tested. Several different zeolites are disclosed for the synthesis of 2,2,6,6-tetramethyl-4-piperidone. It has been found that the most effective zeolite in this regard is a H-Y zeolite having a silica-to-alumina molar ratio of 11.2 achieving a conversion of acetone of 46.2% and a selectivity towards 2,2,6,6-tetramethyl-4-piperidone of 44.1%. In contrast thereto, a H-beta zeolite having a silica-to-alumina molar ratio of 50 achieved a conversion of acetone of 15.8% and a selectivity towards 2,2,6,6-tetramethyl-4-piperidone of 15.3%. Further, only a comparatively low conversion (5.6%) was achieved using a H-ZSM-5 zeolite having a silica-to-alumina molar ratio of 50 where only traces of 2,2,6,6-tetramethyl-4-piperidone were produced. Consequently, J. Tian et al. considered using the H-Y zeolite having the comparatively lowest silica-to-alumina molar ratio and not any of the other zeolites for further experiments as regards the reaction conditions.

Thus, there was the need to develop an improved process for the production of 2,2,6,6-tetramethyl-4-piperidone where the formation of by-products is avoided or at least diminished.

DETAILED DESCRIPTION

Therefore, it was an object of the present invention to provide an improved process for the production of 2,2,6,6-tetramethyl-4-piperidone, in particular as regards an improved selectivity towards 2,2,6,6-tetramethyl-4-piperidone. In particular, it was an object to provide a process where the selectivity towards 2,2,6,6-tetramethyl-4-piperidone is improved over long reaction times. Thus, it was an object to especially avoid or at least diminish the formation of by-products.

Thus, it has surprisingly been found that use of a catalyst comprising a zeolitic material having a specific silica to alumina molar ratio in a heterogeneous process for production of 2,2,6,6-tetramethyl-4-piperidone leads to an improved selectivity towards 2,2,6,6-tetramethyl-4-piperidone, wherein in particular the formation of by-products is reduced. Further and in contrast to a homogenous process, a heterogeneous process allows for a simple recycling since a heterogeneous is easily separated from a reaction mixture which does not have to be separated from a reaction mixture.

Further, it has quite unexpectedly been found that the catalyst does not undergo significant deactivation during the reaction.

Therefore, the present invention relates to a process for the production of 2,2,6,6-tetramethyl-4-piperidone comprising (i) providing a reactor containing a catalyst comprising a zeolitic material having a framework structure selected from the group consisting of EMT, GME, OFF, FER, HEU, MEL, MWW, RRO, TON, FAU, and mixed structures of two or more thereof, wherein the zeolitic material comprises $YO_2$ and $X_2O_3$ in its framework structure, wherein Y is a tetravalent element and X is a trivalent element, wherein the zeolitic material has an $YO_2$ to $X_2O_3$ molar ratio of 12 or greater;

(ii) preparing a reaction mixture comprising acetone and ammonia;

(iii) contacting the catalyst in the reactor with the reaction mixture prepared in (ii) at a temperature in the range of from 40 to 250° C. for obtaining a reaction product comprising 2,2,6,6-tetramethyl-4-piperidone;

wherein the mixture prepared in (ii) and contacted with the catalyst in (iii) contains less than 10 wt.-% of water based on 100 wt.-% of the reaction mixture.

It is preferred that the mixture prepared in (ii) and contacted with the catalyst in (iii) contains less than 8 wt.-%, more preferably less than 6 wt.-%, more preferably less than 4 wt.-%, more preferably less than 2 wt.-%, more preferably less than 1 wt.-%, more preferably less than 0.5 wt.-%, more preferably less than 0.1 wt.-%, more preferably less than 0.05 wt.-%, and more preferably less than 0.01 wt.-% of water based on 100 wt.-% of the reaction mixture.

It is preferred that the zeolitic material has a framework structure selected from the group consisting of EMT, GME, FER, MWW, FAU, and mixed structures of two or more thereof, more preferably from the group consisting of FER, FAU, and a mixed structure thereof, more preferably the zeolitic material has the framework structure FAU.

In an embodiment, the presently claimed invention is directed to the process for the production of 2,2,6,6-tetramethyl-4-piperidone comprising (i) providing a reactor containing a catalyst comprising a zeolitic material having a framework structure of FAU, wherein the zeolitic material comprises $YO_2$ and $X_2O_3$ in its framework structure, wherein Y is a tetravalent element and X is a trivalent element, wherein the zeolitic material has an $YO_2$ to $X_2O_3$ molar ratio of 12 or greater;

(ii) preparing a reaction mixture comprising acetone and ammonia;

(iii) contacting the catalyst in the reactor with the reaction mixture prepared in (ii) at a temperature in the range of from 40 to 250° C. for obtaining a reaction product comprising 2,2,6,6-tetramethyl-4-piperidone;

wherein the mixture prepared in (ii) and contacted with the catalyst in (iii) contains less than 10 wt.-% of water based on 100 wt.-% of the reaction mixture.

It is preferred that from 5 weight-% or more of the catalyst consist of the zeolitic material, more preferably 10 weight-% or more, more preferably 30 weight-% or more, more preferably 50 weight-% or more, more preferably 70 weight-% or more, more preferably 80 weight-% or more, more preferably 90 weight-% or more, more preferably 95 to 100 weight-%, preferably from 99 to 100 weight-%, and more preferably from 99.5 to 100 weight-% of the catalyst consist of the zeolitic material.

It is preferred that the catalyst is provided as a powder and/or as a molding, preferably as an extrudate.

According to the present invention, a molding is to be understood as a three-dimensional entity obtained from a shaping process; accordingly, the term "molding" is used synonymously with the term "shaped body".

It is preferred that Y is selected from the group consisting of Si, Sn, Ti, Zr, Ge, and mixtures of two or more thereof, wherein preferably Y is Si and/or Ti, wherein more preferably Y is Si.

It is preferred that X is selected from the group consisting of B, Al, Ga, In, Sc, Y, La, Ce, Pr, Nd, Pm, Sm, Eu, Gd, Tb, Dy, Ho, Er, Tm, Yb, Lu, and mixtures of two or more thereof, preferably from the group consisting of B, Al, Ga, In, and mixtures of two or more thereof, wherein preferably X is Al and/or B, wherein more preferably X is Al.

In another embodiment, the presently claimed invention is directed to the process for the production of 2,2,6,6-tetramethyl-4-piperidone comprising (i) providing a reactor containing a catalyst comprising a zeolitic material having a framework structure of FAU, wherein the zeolitic material comprises $YO_2$ and $X_2O_3$ in its framework structure, wherein Y is a tetravalent element and X is a trivalent element, wherein the zeolitic material has an $YO_2$ to $X_2O_3$ molar ratio of 16 to 175;

(ii) preparing a reaction mixture comprising acetone and ammonia;

(iii) contacting the catalyst in the reactor with the reaction mixture prepared in (ii) at a temperature in the range of from 40 to 250° C. for obtaining a reaction product comprising 2,2,6,6-tetramethyl-4-piperidone;

wherein the mixture prepared in (ii) and contacted with the catalyst in (iii) contains less than 10 wt.-% of water based on 100 wt.-% of the reaction mixture.

No particular restriction applies as regards the $YO_2$ to $X_2O_3$ molar ratio of $YO_2$ and $X_2O_3$ comprised in the zeolitic material. It is preferred that the zeolitic material has an $YO_2$ to $X_2O_3$ molar ratio of 13 or greater, more preferably in the range of from 13 to 300, preferably of from 14 to 250, more preferably of from 15 to 200, more preferably of from FNMR, more preferably of from 17 to 150, more preferably of from 18 to 125, more preferably of from 19 to 100, more preferably of from 20 to 90, more preferably of from 21 to 80, more preferably of from 22 to 70, more preferably of from 22.5 to 60, more preferably of from 23 to 50, more preferably of from 23.5 to 45, more preferably of from 24 to 40, more preferably of from 24.5 to 37, more preferably of from to 35, more preferably of from 25 to 30.

As disclosed above, it is preferred that the zeolitic material has the FAU framework structure type. It is particularly preferred that in the case where the zeolitic material has the FAU framework structure type the zeolitic material contains one or zeolites having an FAU-type framework structure selected from the group consisting of Li-LSX, zeolite X, zeolite Y, ECR-30, ZSM-20, LZ-210, SAPO-37, US-Y, CSZ-1, ZSM-3, Faujasite, and mixtures of two or more thereof, more preferably from the group consisting of zeolite X, zeolite Y, ECR-30, ZSM-20, LZ-210, US-Y, CSZ-1, ZSM-3, Faujasite, and mixtures of two or more thereof, more preferably from the group consisting of zeolite X, zeolite Y, ZSM-20, ZSM-3, Faujasite, and mixtures of two or more thereof, more preferably from the group consisting of zeolite X, zeolite Y, Faujasite, and mixtures of two or more thereof, wherein more preferably the one or more zeolites having an FAU-type framework structure comprise zeolite X and/or zeolite Y, preferably zeolite Y, wherein more preferably the one or more zeolites having an FAU-type framework structure is zeolite X and/or zeolite Y, preferably zeolite Y.

It is preferred that the zeolitic material is in the ammonium-form or in the H-form, more preferably in the H-form.

No particular restriction applies as regards the chemical or physical nature of the zeolitic material. It is preferred that the zeoltic material comprises a concentration of acid sites in the range of from 0.100 to 4.000 mmol/g at a temperature in the range of from 190 to 550° C., more preferably in the range of from 0.200 to 2.000 mmol/g at a temperature in the range of from 205 to 400° C., more preferably in the range of from 0.250 to 1.000 mmol/g at a temperature in the range of from 250 to 290° C., more preferably in the range of from 0.300 to 0.800 mmol/g at a temperature in the range of from 350 to 375° C., more preferably in the range of from 0.400 to 0.700 mmol/g at a temperature in the range of from 360 to 366° C., preferably as determined by temperature programmed desorption of ammonia ($NH_3$-TPD) [according to Reference example 2].

The temperature-programmed desorption of ammonia ($NH_3$-TPD) is conducted in an automated chemisorption analysis unit (Micromeritics AutoChem II 2920) having a thermal conductivity detector. Continuous analysis of the desorbed species is accomplished using an online mass spectrometer (OmniStar QMG200 from Pfeiffer Vacuum). The sample (0.1 g) is introduced into a quartz tube and analysed using the program described below. The temperature is measured by means of a Ni/Cr/Ni thermocouple immediately above the sample in the quartz tube. For the analyses, He of purity 5.0 is used. Before any measurement, a blank sample is analysed for calibration.

1. Preparation: Commencement of recording; one measurement per second. Wait for 10 minutes at 25° C. and a He flow rate of 30 cm³/min (room temperature (about 25° C.) and 1 atm); heat up to 600° C. at a heating rate of 20 K/min; hold for 10 minutes. Cool down under a He flow (30 cm³/min) to 100° C. at a cooling rate of 20 K/min (furnace ramp temperature); Cool down under a He flow (30 cm³/min) to 100° C. at a cooling rate of 3 K/min (sample ramp temperature).
2. Saturation with $NH_3$: Commencement of recording; one measurement per second. Change the gas flow to a mixture of 10% $NH_3$ in He (75 cm³/min; 100° C. and 1 atm) at 100° C.; hold for 30 min.
3. Removal of the excess: Commencement of recording; one measurement per second. Change the gas flow to a He flow of 75 cm³/min (100° C. and 1 atm) at 100° C.; hold for 60 min.
4. $NH_3$-TPD: Commencement of recording; one measurement per second. Heat up under a He flow (flow rate: 30 cm³/min) to 600° C. at a heating rate of 10 K/min; hold for 30 min.
5. End of measurement.

Desorbed ammonia is measured by means of the online mass spectrometer, which demonstrated that the signal from the thermal conductivity detector is caused by desorbed ammonia. This involved utilizing the m/z=16 signal from ammonia in order to monitor the desorption of the ammonia. The amount of ammonia adsorbed (mmol/g of sample) is ascertained by means of the Micromeritics software through integration of the TPD signal with a horizontal baseline.

Further, it is preferred that the zeolitic material comprises a concentration of acid sites in the range of from 0.050 to 0.600 mmol/g at a temperature in the range of from 175 to 210° C., more preferably in the range of from 0.140 to 0.530 mmol/g at a temperature in the range of from 185 to 200° C., preferably as determined by temperature programmed desorption of ammonia ($NH_3$-TPD) according to reference example 2.

Further, it is preferred that the zeolitic material comprises a concentration of acid sites in the range of from 0.010 to 0.090 mmol/g at a temperature in the range of from 475 to 625° C., more preferably in the range of from 0.030 to 0.060 mmol/g at a temperature in the range of from 500 to 600° C., preferably as determined by temperature programmed desorption of ammonia ($NH_3$-TPD) according to reference example 2.

It is preferred that the zeolitic material has a crystallinity in the range of from 50 to 100 weight-%, more preferably from 75 to 100 weight-%, more preferably from 80 to 100 weight-%, and more preferably from 90 to 100 weight-%, wherein the crystallinity is preferably determined as described in Reference Example 3.

It is preferred that the zeolitic material has a crystallinity in the range of from 50 to 100 weight-%, more preferably from 75 to 100 weight-%, more preferably from 80 to 100 weight-%, and more preferably from 90 to 100 weight-%, wherein the crystallinity is preferably determined by powder X-ray diffraction (PXRD) using a using a diffractometer (D8 Advance Series II, Bruker AXS GmbH) equipped with a LYNXEYE detector operated with a Copper anode X-ray tube running at 40 kV and 40 mA. The geometry is Bragg-Brentano, and air scattering is reduced using an air scatter shield. The crystallinity of the samples is determined using the software DIFFRAC.EVA provided by Bruker AXS GmbH, Karlsruhe. The phase composition is computed against the raw data using the modelling software DIFFRAC.TOPAS provided by Bruker AXS GmbH, Karlsruhe. The crystal structures of the identified phases, instrumental parameters as well the crystallite size of the individual phases are used to simulate the diffraction pattern. This is fit against the data in addition to a function modelling the background intensities. The samples are homogenized in a mortar and then pressed into a standard flat sample holder provided by Bruker AXS GmbH for Bragg-Brentano geometry data collection. The flat surface is achieved using a glass plate to compress and flatten the sample powder. The data is collected from the angular range 2 to 70° 2 Theta with a step size of 0.02° 2 Theta, while the variable divergence slit is set to an angle of 0.1°. The crystalline content describes the intensity of the crystalline signal to the total scattered intensity.

It is preferred that the zeolitic material has a volume-based particle size distribution characterized by a Dv50 value in the range of from 4.0 to 7.0 micrometer, more preferably in the range of from 4.5 to 6.5 micrometer, more preferably in the range of from 5.0 to 6.0 micrometer.

As regards the content of $YO_2$, calculated as the element Y, contained in the zeolitic material, no particular restriction applies. It is preferred that $YO_2$, calculated as the element Y, is contained in the zeolitic material in the range of from 35.0 to 47.0 weight-%, more preferably in the range of from 38.5 to 43.5 weight-%, more preferably in the range of from 40.0 to 42.0 weight-%, based on the total weight of the zeolitic material.

As regards the content of $X_2O_3$, calculated as X, contained in the zeolitic material, no particular restriction applies. It is preferred that $X_2O_3$, calculated as X, is contained in the zeolitic material in the range of from 1.0 to 4.5 weight-%, more preferably in the range of from 2.2 to 3.7 weight-%, more preferably in the range of from 2.9 to 3.3 weight-%, based on the total weight of the zeolitic material.

It is preferred that the zeolitic material has a BET specific surface area equal or greater than 380 m²/g, more preferably equal or greater than 650 m²/g, more preferably in the range of from 700 to 800 m²/g, preferably determined as described in Reference Example 1.

It is preferred that the zeolitic material has a BET specific surface area equal or greater than 380 m²/g, more preferably equal or greater than 650 m²/g, more preferably in the range of from 700 to 800 m²/g, preferably determined via nitrogen physisorption at 77 K according to the method disclosed in DIN 66131.

It is preferred that the zeolitic material has a Langmuir specific surface area equal or greater than 500 m²/g, more preferably equal or greater than 800 m²/g, more preferably in the range of from 810 to 1100 m²/g, preferably determined as described in Reference Example 1.

As disclosed above, it is preferred that X comprises, preferably is, Al. In the case where X comprises, preferably is, Al, it is preferred that the solid state $^{27}$Al NMR of the zeolitic material shows a peak in the range of from 80 to 40 ppm and a peak in the range of from 40 to 15 ppm, wherein the ratio of the peak integral of the peak in the range of from 80 to 40 ppm to the peak integral of the peak in the range of from 40 to 15 ppm is at least 3:1, more preferably at least 7:1, more preferably at least 10:1, preferably determined as described in Reference Example 4.

As disclosed above, it is preferred that X comprises, preferably is, Al. In the case where X comprises, preferably is, Al, it is preferred that the solid state $^{27}$Al NMR of the zeolitic material shows a peak in the range of from 80 to 40 ppm and a peak in the range of from 40 to 15 ppm, wherein the ratio of the peak integral of the peak in the range of from 80 to 40 ppm to the peak integral of the peak in the range of from 40 to 15 ppm is at least 3:1, more preferably at least 7:1, more preferably at least 10:1, preferably determined via $^{27}$Al solid-state nuclear magnetic resonance (NMR).

$^{27}$Al solid-state nuclear magnetic resonance (NMR) is performed by storage of samples at 62% relative humidity for at least 60 hours prior to packing; packing of samples into 3.2 mm ZrO$_2$ rotors with Vespel caps, Bruker Avance Neo spectrometer with 14.1 Tesla magnet, 15 kHz ($\omega/2\pi$) magic angle spinning, one-pulse radiofrequency excitation corresponding to a 0.92 µs 15°-pulse on AlCl$_3$-solution (1% in H$_2$O); 10 ms acquisition of the free induction decay, no heteronuclear $^1$H radiofrequency decoupling, averaging of at least 5120 scans with a recycle delay of 0.5 s, Fourier transform with 10 Hz exponential line broadening for noise suppression, manual phasing and baseline correction in Bruker Topspin 3.0. Spectra are referenced relative to Al(NO$_3$)$_3$ in D$_2$O, 1.1 mol/kg at a frequency ratio of 0.26056859 on the absolute chemical shift scale, according to Pure Appl. Chem., Vol. 80, No. 1, pp. 59-84, 2008, using adamantane with a $^{13}$C methylene resonance at 37.77 ppm as a secondary standard.

Further in the case where X comprises, preferably is, Al, it is preferred that the solid state $^{27}$Al NMR of the zeolitic material shows a peak in the range of from 80 to 40 ppm and a peak in the range of from 15 to −20 ppm, wherein the ratio of the peak integral of the peak in the range of from 80 to 40 ppm to the peak integral of the peak in the range of from 15 to −20 ppm is at least 3:1, more preferably at least 7:1, more preferably at least 10:1, preferably determined as described in Reference Example 4.

It is preferred that the zeolitic material has a micropore volume in the range of from 0.180 to 0.390 ml/g, more preferably of from 0.220 to 0.350 ml/g, more preferably of from 0.260 to 0.310 ml/g, preferably determined as described in Reference Example 1.

It is preferred that the zeolitic material has an average pore diameter in the range of from 4.0 to 18.0 nm, more preferably of from 5.5 to 8.0 nm, more preferably of from 6.6 to 7.3 nm, preferably determined as described in Reference Example 1.

It is preferred that the zeolitic material has an average pore width in the range of from 1.5 to 5.5 nm, more preferably of from 2.0 to 3.5 nm, more preferably of from 2.4 to 2.8 nm, preferably determined as described in Reference Example 1.

It is preferred that the zeolitic material provided in (i) is a calcined zeolitic material, wherein the zeolitic material has been calcined at a temperature in the range of from 300 to 900° C., more preferably of from 400 to 700° C., more preferably of from 450 to 650° C., and more preferably of from 500 to 600° C.

Depending on the mass of the precursor of the molding to be calcined, the duration of calcining should have been adjusted. It is preferred that the zeolitic material has been calcined for a duration of from 0.5 to 24 h, more preferably from 1 to 15 h, more preferably from 2 to 12 h, more preferably from 2.5 to 9 h, more preferably from 3 to 7 h, more preferably from 3.5 to 6.5 h, and more preferably from 4 to 6 h.

As regards further process steps, no particular restriction applies. It is preferred that the catalyst is washed with acetone prior to contacting of the catalyst with the reaction mixture in (ii). It is preferred that prior to contacting of the catalyst with the reaction mixture in (ii) the catalyst is first contacted with acetone.

As regards the temperature at which in (iii) the contacting of the catalyst with the reaction mixture prepared in (ii) is conducted, no particular restriction applies. It is preferred that in (iii) the contacting of the catalyst with the reaction mixture prepared in (ii) is conducted at a temperature in the range of from 45 to 200° C., more preferably from 50 to 150° C., more preferably from 55 to 120° C., more preferably from 60 to 100° C., more preferably in the range of from 65 to 90° C., and more preferably in the range of from 70 to 80° C.

As regards the pressure at which in (iii) the contacting of the catalyst with the reaction mixture prepared in (ii) is conducted, no particular restriction applies. It is preferred that in (iii) the contacting of the catalyst with the reaction mixture prepared in (ii) is conducted at a pressure in the range of from 1 to 200 bar(abs), more preferably in the range of from 20 to 150 bar(abs), more preferably in the range of from 30 to 100 bar(abs), more preferably in the range of from 45 to 80 bar(abs), more preferably in the range of from 50 to 70, more preferably in the range of from 55 to 65 bar(abs).

As disclosed above, no particular restriction applies as regards the pressure at which in (iii) the contacting of the catalyst with the reaction mixture prepared in (ii) is conducted. It is preferred that in (iii) the contacting of the catalyst with the reaction mixture prepared in (ii) is conducted at a pressure in the range of from 1 to 30 bar(abs), more preferably in the range of from 1 to 20 bar(abs), more preferably in the range of from 1 to 15 bar(abs), more preferably in the range of from 1 to 10 bar(abs), more preferably in the range of from 1 to 5, more preferably in the range of from 1 to 3 bar(abs).

It is preferred that the process is conducted as a batch process or as a continuous process. It is particularly preferred that the process is conducted as a continuous process.

As disclosed above, it is preferred that the process is conducted as a continuous process. In the case where the process is conducted as a continuous process, it is preferred that contacting in (iii) is conducted at a liquid hourly space velocity (LHSV) in the range of from 0.01 to 1000 ml/(g·h), more preferably from 0.05 to 500 ml/(g·h), more preferably from 0.1 to 250 ml/(g·h), more preferably from 0.3 to 100 ml/(g·h), more preferably from 0.5 to 10 ml/(g·h), more preferably from 1 to 5 ml/(g·h), more preferably from 1.2 to 4 ml/(g·h), more preferably from 1.5 to 3 ml/(g·h), more preferably from 1.8 to 2.5 ml/(g·h), more preferably from 2.0 to 2.2 ml/(g·h).

As disclosed above, the process may comprise further process steps. It is preferred that the process further comprises (iv) separating 2,2,6,6-tetramethyl-4-piperidone from the reaction product to obtain 2,2,6,6-tetramethyl-4-piperidone and a residual mixture;

(v) recycling at least a portion of the residual mixture in the reaction mixture in (ii), wherein preferably after (iv) and prior to (v) compounds having a boiling point higher than that of 2,2,6,6-tetramethyl-4-piperidone were separated from the residual mixture.

As regards the molar ratio of acetone to ammonia in the reaction mixture prepared in (ii), no particular restriction applies. It is preferred that in the reaction mixture prepared in (ii), the molar ratio of acetone to ammonia is in the range of from 5:1 to 25:1, more preferably of from 7:1 to 22:1, more preferably of from 10:1 to 19:1, more preferably of from 13:1 to 16:1, more preferably in the range of from 14.0:1.0 to 14.7:1.0, more preferably in the range of from 14.2:1.0 to 14.5:1.0.

As disclosed above, the process may be carried out as a batch process. In the case where the process is conducted as a batch process, it is preferred that contacting in (iii) is carried out for a duration in the range of from 0.1 to 24 h, more preferably in the range of from 0.5 to 20 h, more preferably in the range of from 1 to 15 h, more preferably in the range of from 3 to 10 h, more preferably in the range of from 4 to 8 h, more preferably in the range of from 5 to 7 h.

As disclosed above, the catalyst may be provided as a molding. In the case where the catalyst is provided as a molding, it is preferred that the molding is prepared according to a process comprising (a) preparing a mixture comprising the zeolitic material and optionally one or more binders;

(b) shaping the mixture, preferably by extruding to obtain a shaped material;

(c) optionally drying the shaped material in a gas atmosphere;

(d) calcining the shaped material obtained from (b) or (c) in a gas atmosphere to obtain the molding.

In the case where the process comprises (a), (b), (c), and (d) as disclosed above, it is preferred that the mixture comprises one or more binders, wherein the one or more binders is one or more of alumina, silica, silica-alumina, graphite, a polysaccharide, a sugar alcohol and a synthetic polymer, more preferably one or more of alumina, silica, silica-alumina, graphite, a sugar alcohol, a synthetic polymer, cellulose, a modified cellulose and a starch, more preferably silica, alumina, silica-alumina, graphite, a sugar alcohol, a synthetic polymer, a microcrystalline cellulose, a cellulose ether, more preferably graphite, sorbitol, mannitol, polyethylene glycol (PEG), polyvinylpyrrolidone (PVP), hydroxypropyl cellulose (HPC), hydroxypropyl methylcellulose (HPMC), and sodium carboxymethyl cellulose.

Further in the case where the process comprises (a), (b), (c), and (d) as disclosed above, it is preferred that in the mixture according to (a), the weight ratio of the one or more binders relative to the zeolitic material is in the range of from 1:10 to 1:30, more preferably in the range of from 1:15 to 1:25.

Further in the case where the process comprises (a), (b), (c), and (d) as disclosed above, it is preferred that the process comprises drying according to (c), wherein drying is conducted in a gas atmosphere having a temperature in the range of from 90 to 150° C., more preferably at a temperature in the range of from 110 to 130° C., wherein preferably the drying is conducted for 10 to 15 h, more preferably for 11 to 13 h.

Further in the case where the process comprises (a), (b), (c), and (d) as disclosed above, it is preferred that the gas atmosphere in (d) has a temperature in the range of from 400 to 600° C., more preferably in the range of from 450 to 550° C., wherein preferably the calcining is conducted for 3 to 7 h, more preferably for 4 to 6 h.

Further in the case where the process comprises (a), (b), (c), and (d) as disclosed above, it is preferred that the gas atmosphere in one or more of (c) and (d) comprises one or more of nitrogen, oxygen, and argon, preferably nitrogen.

Within the meaning of the present invention, a specific value of relative humidity is not particularly restricting with respect to the atmosphere which displays said specific value in relative humidity such that in principle the value may relate to any suitable atmosphere displaying said value in relative humidity such as e.g. air or an atmosphere of an inert gas such as nitrogen, argon, or mixtures thereof. According to the present invention it is however preferred that a specific relative humidity refers to the relative humidity of an atmosphere selected among the group consisting of air, nitrogen, argon, and mixtures of two or more thereof, wherein more preferably the specific relative humidity refers to an atmosphere of nitrogen and/or argon displaying said level of relative humidity, more preferably to an atmosphere of nitrogen displaying said specific level in relative humidity.

According to the present invention, a molding is to be understood as a three-dimensional entity obtained from a shaping process; accordingly, the term "molding" is used synonymously with the term "shaped body".

The unit bar(abs) refers to an absolute pressure of $10^5$ Pa and the unit Angstrom refers to a length of $10^{-10}$ m.

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4". Further, it is explicitly noted that the following set of embodiments is not the set of claims determining the extent of protection, but represents a suitably structured part of the description directed to general and preferred aspects of the present invention.

1. A process for the production of 2,2,6,6-tetramethyl-4-piperidone comprising
   (i) providing a reactor containing a catalyst comprising a zeolitic material having a framework structure selected from the group consisting of EMT, GME, OFF, FER, HEU, MEL, MWW, RRO, TON, FAU, and mixed structures of two or more thereof, wherein the zeolitic material comprises $YO_2$ and $X_2O_3$ in its framework structure, wherein Y is a tetravalent element and X is a trivalent element, wherein the zeolitic material has an $YO_2$ to $X_2O_3$ molar ratio of 12 or greater;
   (ii) preparing a reaction mixture comprising acetone and ammonia;
   (iii) contacting the catalyst in the reactor with the reaction mixture prepared in (ii) at a temperature in the range of from 40 to 250° C. for obtaining a reaction product comprising 2,2,6,6-tetramethyl-4-piperidone;
   wherein the mixture prepared in (ii) and contacted with the catalyst in (iii) contains less than 10 wt.-% of water based on 100 wt.-% of the reaction mixture, preferably less than 8 wt.-%, more preferably less than 6 wt.-%, more preferably less than 4 wt.-%, more preferably less than 2 wt.-%, more preferably less than 1 wt.-%, more preferably less than 0.5 wt.-%, more preferably less than 0.1 wt.-%, more preferably less than 0.05 wt.-%, and more preferably less than 0.01 wt.-% of water based on 100 wt.-% of the reaction mixture.

2. The process of embodiment 1, wherein the zeolitic material has a framework structure selected from the group consisting of EMT, GME, FER, MWW, FAU, and mixed structures of two or more thereof, preferably from the group consisting of FER, FAU, and a mixed structure thereof, more preferably the zeolitic material has the framework structure FAU.

3. The process of embodiment 1 or 2, wherein from 5 weight-% or more of the catalyst consist of the zeolitic material, preferably 10 weight-% or more, more preferably 30 weight-% or more, more preferably 50 weight-% or more, more preferably 70 weight-% or more, more preferably 80 weight-% or more, more preferably 90 weight-% or more, more preferably 95 to 100 weight-%, preferably from 99 to 100 weight-%, and more preferably from 99.5 to 100 weight-% of the catalyst consist of the zeolitic material.

4. The process of any one of embodiments 1 to 3, wherein the catalyst is provided as a powder and/or as a molding, preferably as an extrudate.

5. The process of any one of embodiments 1 to 4, wherein Y is selected from the group consisting of Si, Sn, Ti, Zr, Ge, and mixtures of two or more thereof, wherein preferably Y is Si and/or Ti, wherein more preferably Y is Si.

6. The process of any one of embodiments 1 to 5, wherein X is selected from the group consisting of B, Al, Ga, In, Sc, Y, La, Ce, Pr, Nd, Pm, Sm, Eu, Gd, Tb, Dy, Ho, Er, Tm, Yb, Lu, and mixtures of two or more thereof, preferably from the group consisting of B, Al, Ga, In, and mixtures of two or more thereof, wherein preferably X is Al and/or B, wherein more preferably X is Al.

7. The process of any one of embodiments 1 to 6, wherein the zeolitic material has an $YO_2$ to $X_2O_3$ molar ratio of 13 or greater, preferably in the range of from 13 to 300, preferably of from 14 to 250, more preferably of from 15 to 200, more preferably of from 16 to 175, more preferably of from 17 to 150, more preferably of from 18 to 125, more preferably of from 19 to 100, more preferably of from 20 to 90, more preferably of from 21 to 80, more preferably of from 22 to 70, more preferably of from 22.5 to 60, more preferably of from 23 to 50, more preferably of from 23.5 to 45, more preferably of from 24 to 40, more preferably of from 24.5 to 37, more preferably of from 25 to 35, more preferably of from 25 to 30.

8. The process of any one of embodiments 1 to 7, wherein the process for the production of 2,2,6,6-tetramethyl-4-piperidone comprising
   (i) providing a reactor containing a catalyst comprising a zeolitic material having a framework structure of FAU, wherein the zeolitic material comprises $YO_2$ and $X_2O_3$ in its framework structure, wherein Y is a tetravalent element and X is a trivalent element, wherein the zeolitic material has an $YO_2$ to $X_2O_3$ molar ratio of 16 to 175;
   (ii) preparing a reaction mixture comprising acetone and ammonia;
   (iii) contacting the catalyst in the reactor with the reaction mixture prepared in (ii) at a temperature in the range of from 40 to 250° C. for obtaining a reaction product comprising 2,2,6,6-tetramethyl-4-piperidone;
   wherein the mixture prepared in (ii) and contacted with the catalyst in (iii) contains less than 10 wt.-% of water based on 100 wt.-% of the reaction mixture.

9. The process of any one of embodiments 1 to 8, wherein the zeolitic material has the FAU framework structure type, wherein preferably the zeolitic material contains one or zeolites having an FAU-type framework structure selected from the group consisting of Li-LSX, zeolite X, zeolite Y, ECR-30, ZSM-20, LZ-210, SAPO-37, US-Y, CSZ-1, ZSM-3, Faujasite, and mixtures of two or more thereof,
   preferably from the group consisting of zeolite X, zeolite Y, ECR-30, ZSM-20, LZ-210, US-Y, CSZ-1, ZSM-3, Faujasite, and mixtures of two or more thereof, more preferably from the group consisting of zeolite X, zeolite Y, ZSM-20, ZSM-3, Faujasite, and mixtures of two or more thereof,
   more preferably from the group consisting of zeolite X, zeolite Y, Faujasite, and mixtures of two or more thereof,
   wherein more preferably the one or more zeolites having an FAU-type framework structure comprise zeolite X and/or zeolite Y, preferably zeolite Y,
   wherein more preferably the one or more zeolites having an FAU-type framework structure is zeolite X and/or zeolite Y, preferably zeolite Y.

10. The process of any one of embodiments 1 to 9, wherein the zeolitic material is in the ammonium-form or in the H-form, preferably in the H-form.

11. The process of any one of embodiments 1 to 10, wherein the zeoltic material comprises a concentration of acid sites in the range of from 0.100 to 4.000 mmol/g at a temperature in the range of from 190 to 550° C., preferably in the range of from 0.200 to 2.000 mmol/g at a temperature in the range of from 205 to 400° C., more preferably in the range of from 0.250 to 1.000 mmol/g at a temperature in the range of from 250 to 290° C., more preferably in the range of from 0.300 to 0.800 mmol/g at a temperature in the range of from 350 to 375° C., more preferably in the range of from 0.400 to 0.700 mmol/g at a temperature in the range of from 360 to 366° C., preferably as determined by temperature programmed desorption of ammonia ($NH_3$-TPD) according to reference example 2.

12. The process of any one of embodiments 1 to 11, wherein the zeolitic material comprises a concentration of acid sites in the range of from 0.050 to 0.600 mmol/g at a temperature in the range of from 175 to 210° C., preferably in the range of from 0.140 to 0.530 mmol/g at a temperature in the range of from 185 to 200° C., preferably as determined by temperature programmed desorption of ammonia ($NH_3$-TPD) according to reference example 2.

13. The process of any one of embodiments 1 to 12, wherein the zeolitic material comprises a concentration of acid sites in the range of from 0.010 to 0.090 mmol/g at a temperature in the range of from 475 to 625° C., preferably in the range of from 0.030 to 0.060 mmol/g at a temperature in the range of from 500 to 600° C., preferably as determined by temperature programmed desorption of ammonia ($NH_3$-TPD) according to reference example 2.

14. The process of any one of embodiments 1 to 13, wherein the zeolitic material has a crystallinity in the range of from 50 to 100 weight-%, preferably from 75 to 100 weight-%, more preferably from 80 to 100 weight-%, and more preferably from 90 to 100 weight-%, wherein the crystallinity is preferably determined as described in Reference Example 3.

15. The process of any one of embodiments 1 to 14, wherein the zeolitic material has a volume-based particle size distribution characterized by a Dv50 value in the range of from 4.0 to 7.0 micrometer, preferably in the range of from 4.5 to 6.5 micrometer, more preferably in the range of from 5.0 to 6.0 micrometer.

16. The process of any one of embodiments 1 to 15, wherein $YO_2$, calculated as the element Y, is contained in the zeolitic material in the range of from 35.0 to 47.0 weight-%, preferably in the range of from 38.5 to 43.5 weight-%, more preferably in the range of from 40.0 to 42.0 weight-%, based on the total weight of the zeolitic material.

17. The process of any one of embodiments 1 to 16, wherein $X_2O_3$, calculated as X, is contained in the zeolitic material in the range of from 1.0 to 4.5 weight-%, preferably in the range of from 2.2 to 3.7 weight-%, more preferably in the range of from 2.9 to 3.3 weight-%, based on the total weight of the zeolitic material.

18. The process of any one of embodiments 1 to 17, wherein the zeolitic material has a BET specific surface area equal or greater than 380 $m^2/g$, preferably equal or greater than 650 $m^2/g$, more preferably in the range of from 700 to 800 $m^2/g$, preferably determined as described in Reference Example 1.

19. The process of any one of embodiments 1 to 18, wherein the zeolitic material has a Langmuir specific surface area equal or greater than 500 $m^2/g$, preferably equal or greater than 800 $m^2/g$, more preferably in the range of from 810 to 1100 $m^2/g$, preferably determined as described in Reference Example 1.

20. The process of any one of embodiments 1 to 19, wherein X is Al, and wherein the solid state $^{27}Al$ NMR of the zeolitic material shows a peak in the range of from 80 to 40 ppm and a peak in the range of from 40 to 15 ppm, wherein the ratio of the peak integral of the peak in the range of from 80 to 40 ppm to the peak integral of the peak in the range of from 40 to 15 ppm is at least 3:1, preferably at least 7:1, more preferably at least 10:1, preferably determined as described in Reference Example 4.

21. The process of any one of embodiments 1 to 20, wherein X is Al, and wherein the solid state $^{27}Al$ NMR of the zeolitic material shows a peak in the range of from 80 to 40 ppm and a peak in the range of from 15 to −20 ppm, wherein the ratio of the peak integral of the peak in the range of from 80 to 40 ppm to the peak integral of the peak in the range of from 15 to −20 ppm is at least 3:1, preferably at least 7:1, more preferably at least 10:1, preferably determined as described in Reference Example 4.

22. The process of any one of embodiments 1 to 21, wherein the zeolitic material has a micropore volume in the range of from 0.180 to 0.390 ml/g, preferably of from 0.220 to 0.350 ml/g, more preferably of from 0.260 to 0.310 ml/g, preferably determined as described in Reference Example 1.

23. The process of any one of embodiments 1 to 22, wherein the zeolitic material has an average pore diameter in the range of from 4.0 to 18.0 nm, preferably of from 5.5 to 8.0 nm, more preferably of from 6.6 to 7.3 nm, preferably determined as described in Reference Example 1.

24. The process of any one of embodiments 1 to 23, wherein the zeolitic material has an average pore width in the range of from 1.5 to 5.5 nm, preferably of from 2.0 to 3.5 nm, more preferably of from 2.4 to 2.8 nm, preferably determined as described in Reference Example 1.

25. The process of any one of embodiments 1 to 24, wherein the zeolitic material provided in (i) is a calcined zeolitic material, wherein the zeolitic material has been calcined at a temperature in the range of from 300 to 900° C., preferably of from 400 to 700° C., more preferably of from 450 to 650° C., and more preferably of from 500 to 600° C.

26. The process of embodiment 25, wherein the zeolitic material has been calcined for a duration of from 0.5 to 24 h, preferably from 1 to 15 h, more preferably from 2 to 12 h, more preferably from 2.5 to 9 h, more preferably from 3 to 7 h, more preferably from 3.5 to 6.5 h, and more preferably from 4 to 6 h.

27. The process of any one of embodiments 1 to 26, wherein prior to contacting of the catalyst with the reaction mixture in (ii) the catalyst is first contacted with acetone.

28. The process of any one of embodiments 1 to 27, wherein in (iii) the contacting of the catalyst with the reaction mixture prepared in (ii) is conducted at a temperature in the range of from 45 to 200° C., preferably from 50 to 150° C., more preferably from 55 to 120° C., more preferably from 60 to 100° C., more preferably in the range of from 65 to 90° C., and more preferably in the range of from 70 to 80° C.

29. The process of any one of embodiments 1 to 28, wherein in (iii) the contacting of the catalyst with the reaction mixture prepared in (ii) is conducted at a pressure in the range of from 1 to 200 bar(abs), preferably in the range of from 20 to 150 bar(abs), more preferably in the range of from 30 to 100 bar(abs), more preferably in the range of from 45 to 80 bar(abs), more preferably in the range of from 50 to 70, more preferably in the range of from 55 to 65 bar(abs).

30. The process of any one of embodiments 1 to 28, wherein in (iii) the contacting of the catalyst with the reaction mixture prepared in (ii) is conducted at a pressure in the range of from 1 to 30 bar(abs), preferably in the range of from 1 to 20 bar(abs), more preferably in the range of from 1 to 15 bar(abs), more preferably in the range of from 1 to 10 bar(abs), more preferably in the range of from 1 to 5, more preferably in the range of from 1 to 3 bar(abs).

31. The process of any one of embodiments 1 to 30, wherein the process is conducted as a batch process or as a continuous process, wherein preferably the process is conducted as a continuous process.

32. The process of any one of embodiments 1 to 31, wherein the process is conducted as a continuous process, and wherein contacting in (iii) is conducted at a liquid hourly space velocity (LHSV) in the range of from 0.01 to 1000 ml/(g·h), preferably from 0.05 to 500 ml/(g·h), more preferably from 0.1 to 250 ml/(g·h), more preferably from 0.3 to 100 ml/(g·h), more preferably from 0.5 to 10 ml/(g·h), more preferably from 1 to 5 ml/(g·h), more preferably from 1.2 to 4 ml/(g·h), more preferably from 1.5 to 3 ml/(g·h), more preferably from 1.8 to 2.5 ml/(g·h), more preferably from 2.0 to 2.2 ml/(g·h).

33. The process of any one of embodiments 1 to 32, wherein the process further comprises
    (iv) separating 2,2,6,6-tetramethyl-4-piperidone from the reaction product to obtain 2,2,6,6-tetramethyl-4-piperidone and a residual mixture;
    (v) recycling at least a portion of the residual mixture in the reaction mixture in (ii), wherein preferably after (iv) and prior to (v) compounds having a boiling point higher than that of 2,2,6,6-tetramethyl-4-piperidone were separated from the residual mixture.

34. The process of any one of embodiments 1 to 33, wherein in the reaction mixture prepared in (ii), the molar ratio of acetone to ammonia is in the range of from 5:1 to 25:1, preferably of from 7:1 to 22:1, more preferably of from 10:1 to 19:1, more preferably of from 13:1 to 16:1, more preferably in the range of from 14.0:1.0 to 14.7:1.0, more preferably in the range of from 14.2:1.0 to 14.5:1.0.

35. The process of any one of embodiments 1 to 34, wherein the process is conducted as a batch process, wherein contacting in (iii) is carried out for a duration in the range of from 0.1 to 24 h, preferably in the range of from 0.5 to 20 h, more preferably in the range of from 1 to 15 h, more preferably in the range of from 3 to 10 h, more preferably in the range of from 4 to 8 h, more preferably in the range of from 5 to 7 h.

36. The process of any one of embodiments 1 to 35, wherein the catalyst is provided as a molding, wherein the molding is prepared according to a process comprising
    (a) preparing a mixture comprising the zeolitic material and optionally one or more binders;
    (b) shaping the mixture, preferably by extruding to obtain a shaped material;
    (c) optionally drying the shaped material in a gas atmosphere;
    (d) calcining the shaped material obtained from (b) or (c) in a gas atmosphere to obtain the molding.

37. The process of embodiment 36, wherein the mixture comprises one or more binders, wherein the one or more binders is one or more of alumina, silica, silica-alumina, graphite, a polysaccharide, a sugar alcohol and a synthetic polymer, preferably one or more of alumina, silica, silica-alumina, graphite, a sugar alcohol, a synthetic polymer, cellulose, a modified cellulose and a starch, more preferably silica, alumina, silica-alumina, graphite, a sugar alcohol, a synthetic polymer, a microcrystalline cellulose, a cellulose ether, more preferably graphite, sorbitol, mannitol, polyethylene glycol (PEG), polyvinylpyrrolidone (PVP), hydroxypropyl cellulose (HPC), hydroxypropyl methylcellulose (HPMC), and sodium carboxymethyl cellulose.

38. The process of embodiment 36 or 37, wherein in the mixture according to (a), the weight ratio of the one or more binders relative to the zeolitic material is in the range of from 1:10 to 1:30, preferably in the range of from 1:15 to 1:25.

39. The process of any one of embodiments 36 to 38, wherein the process comprises drying according to (c), wherein drying is conducted in a gas atmosphere having a temperature in the range of from 90 to 150° C., preferably at a temperature in the range of from 110 to 130° C., wherein preferably the drying is conducted for 10 to 15 h, more preferably for 11 to 13 h.

40. The process of any one of embodiments 36 to 39, wherein the gas atmosphere in (d) has a temperature in the range of from 400 to 600° C., preferably in the range of from 450 to 550° C., wherein preferably the calcining is conducted for 3 to 7 h, more preferably for 4 to 6 h.

41. The process of any one of embodiments 36 to 40, wherein the gas atmosphere in one or more of (c) and (d) comprises one or more of nitrogen, oxygen, and argon, preferably nitrogen.

EXAMPLES

Reference Example 1: Determination of the BET Specific Surface Area, the Langmuir Specific Surface Area, the Micropore Volume, the Average Pore Width and the Average Pore Diameter ($N_2$)

The BET specific surface area, the Langmuir specific surface area, the micropore volume, the average pore width and the average pore diameter ($N_2$) were determined via nitrogen physisorption at 77 K according to the method disclosed in DIN 66131.

Reference Example 2: Determination of the Acid Sites: Temperature Programmed Desorption of Ammonia ($NH_3$-TPD)

The temperature-programmed desorption of ammonia ($NH_3$-TPD) was conducted in an automated chemisorption analysis unit (Micromeritics AutoChem 2920) having a thermal conductivity detector. Continuous analysis of the desorbed species was accomplished using an online mass spectrometer (OmniStar QMG200 from Pfeiffer Vacuum). The sample (0.1 g) was introduced into a quartz tube and analysed using the program described below. The temperature was measured by means of a Ni/Cr/Ni thermocouple immediately above the sample in the quartz tube. For the analyses, He of purity 5.0 was used. Before any measurement, a blank sample was analysed for calibration.
1. Preparation: Commencement of recording; one measurement per second. Wait for 10 minutes at 25° C. and a He flow rate of 30 cm$^3$/min (room temperature (about 25° C.) and 1 atm); heat up to 600° C. at a heating rate of 20 K/min; hold for 10 minutes. Cool down under a He flow (30 cm$^3$/min) to 100° C. at a cooling rate of 20 K/min (furnace ramp temperature); Cool down under a He flow (30 cm$^3$/min) to 100° C. at a cooling rate of 3 K/min (sample ramp temperature).
2. Saturation with $NH_3$: Commencement of recording; one measurement per second. Change the gas flow to a mixture of 10% $NH_3$ in He (75 cm$^3$/min; 100° C. and 1 atm) at 100° C.; hold for 30 min.
3. Removal of the excess: Commencement of recording; one measurement per second. Change the gas flow to a He flow of 75 cm$^3$/min (100° C. and 1 atm) at 100° C.; hold for 60 min.
4. $NH_3$-TPD: Commencement of recording; one measurement per second. Heat up under a He flow (flow rate: 30 cm$^3$/min) to 600° C. at a heating rate of 10 K/min; hold for 30 min.
5. End of measurement.

Desorbed ammonia was measured by means of the online mass spectrometer, which demonstrated that the signal from the thermal conductivity detector was caused by desorbed ammonia.

This involved utilizing the m/z=16 signal from ammonia in order to monitor the desorption of the ammonia. The amount of ammonia adsorbed (mmol/g of sample) was ascertained by means of the Micromeritics software through integration of the TPD signal with a horizontal baseline.

Reference Example 3: X-Ray Powder Diffraction and Determination of the Crystallinity Powder X-ray diffraction (PXRD) data was collected using a diffractometer (D8 Advance Series II, Bruker AXS GmbH) equipped with a LYNXEYE detector operated with a Copper anode X-ray tube running at 40 kV and 40 mA. The geometry was Bragg-Brentano, and air scattering was reduced using an air scatter shield.

Computing crystallinity: The crystallinity of the samples was determined using the software DIFFRAC.EVA provided by Bruker AXS GmbH, Karlsruhe. The method is described on page 121 of the user manual. The default parameters for the calculation were used.

Computing phase composition: The phase composition was computed against the raw data using the modelling software DIFFRAC.TOPAS provided by Bruker AXS GmbH, Karlsruhe. The crystal structures of the identified phases, instrumental parameters as well the crystallite size of the individual phases were used to simulate the diffraction pattern. This was fit against the data in addition to a function modelling the background intensities.

Data collection: The samples were homogenized in a mortar and then pressed into a standard flat sample holder provided by Bruker AXS GmbH for Bragg-Brentano geometry data collection. The flat surface was achieved using a glass plate to compress and flatten the sample powder. The data was collected from the angular range 2 to 70° 2 Theta with a step size of 0.02° 2 Theta, while the variable divergence slit was set to an angle of 0.1°. The crystalline content describes the intensity of the crystalline signal to the total scattered intensity. (User Manual for DIFFRAC.EVA, Bruker AXS GmbH, Karlsruhe.)

Reference Example 4: Determination of Solid State $^{27}$Al NMR $^{27}$Al solid-state nuclear magnetic resonance (NMR) was performed using the following devices, procedures and parameters: Storage of samples at 62% relative humidity for at least 60 hours prior to packing; packing of samples into 3.2 mm $ZrO_2$ rotors with Vespel caps, Bruker Avance Neo spectrometer with 14.1 Tesla magnet, 15 kHz ($\omega/2\pi$) magic angle spinning, one-pulse radiofrequency excitation corresponding to a 0.92 µs 15°-pulse on $AlCl_3$-solution (1% in $H_2O$); 10 ms acquisition of the free induction decay, no heteronuclear $^1$H radiofrequency decoupling, averaging of at least 5120 scans with a recycle delay of 0.5 s, Fourier transform with 10 Hz exponential line broadening for noise suppression, manual phasing and baseline correction in Bruker Topspin 3.0. Spectra were referenced relative to $Al(NO_3)_3$ in $D_2O$, 1.1 mol/kg at a frequency ratio of 0.26056859 on the absolute chemical shift scale, according to Pure Appl. Chem., Vol. 80, No. 1, pp. 59-84, 2008, using adamantane with a $^{13}$C methylene resonance at 37.77 ppm as a secondary standard.

Reference Example 5: Characteristics of the Tested Zeolitic Materials

TABLE 1

Part I of the characteristics for the tested zeolitic materials

| Catalyst | Zeolite | SAR | crystallinity | Elemental analysis | BET s. a. [m$^2$/g] | Langmuir s. a. [m$^2$/g] |
|---|---|---|---|---|---|---|
| Comp. 1 | H-zeolite Y (HSZ-330HUA, Tosoh) | 6 | — | — | 607 | 790 |
| Comp. 2 | H-zeolite Y (HSZ-330HUA, Tosoh) | 6 | — | — | 577 | 750 |
| Comp. 3 | NH$_4$-zeolite Y (CBV 500, Zeolyst) | 5.2 | — | — | 625 | 816 |
| Comp. 4 | Zeolite beta (calcined) | 10 | | | 649 | 850 |
| Comp. 5 | Mordenite | 15 | 84 | 5.1 wt.-% Al 40.0 wt.-% Si | 447 | 582 |
| Comp. 6 | ZSM-5 (calcined) | 30 | 81 | 2.5 wt.-% Al 41.0 wt.-% Si 0.01 wt.-% C | 381 | 501 |
| 1 | H-zeolite Y (DY-32, Evertruth) | 25 | 95 | 3.1 wt.-% Al 41.0 wt.-% Si | 788 | 1030 |
| 2 | H-zeolite Y (DY-32, Evertruth) | 25 | 93 | 3.1 wt.-% Al 41.0 wt.-% Si | 750 | 980 |
| 3 | H-zeolite Y (DY-43, Evertruth) | 34 | 95 | 2.3 wt.-% Al 41.0 wt.-% Si | 727 | 949 |
| 4 | H-zeolite Y (Evertruth) | 20 | 93 | 3.5 wt.-% Al 39 wt.-% Si | 770 | 1034 |

TABLE 2

Part II of the characteristics for the tested zeolitic materials

| Catalyst | Micropore vol. [ml/g] | Average pore width [nm] | Average pore diameter (N$_2$) [nm] | NH$_3$—TPD (T$_{max}$; mmol/g) |
|---|---|---|---|---|
| Comp. 1 | 0.242 | 2.53 | 8.92 | 196; 0.511 355; 0.607 589; 0.037 |
| Comp. 2 | 0.231 | 2.63 | 10.25 | |
| Comp. 3 | 0.256 | 2.24 | 5.91 | |
| Comp. 4 | 0.230 | 4.30 | 16.84 | |
| Comp. 5 | 0.185 | 2.10 | 5.97 | |
| Comp. 6 | 0.121 | 2.89 | 7.35 | |
| 1 | 0.297 | 2.56 | 6.70 | 193; 0.285 365; 0.649 576; 0.056 |
| 2 | 0.287 | 2.54 | 6.80 | |
| 3 | 0.278 | 2.72 | 7.18 | 188; 0.151 361; 0.475 527; 0.052 |

TABLE 2-continued

Part II of the characteristics for the tested zeolitic materials

| Catalyst | Micropore vol. [ml/g] | Average pore width [nm] | Average pore diameter (N$_2$) [nm] | NH$_3$—TPD (T$_{max}$; mmol/g) |
|---|---|---|---|---|
| 4 | 0.292 | 2.50 | 8.20 | 199; 0.336 |
|   |       |      |      | 369; 0.796 |
|   |       |      |      | 579; 0.045 |

Example 1: Catalytic Testing—Batch Mode

Catalysts 1 and 4, and Comparative catalysts 1 and 3 have been tested as catalyst for the production of 2,2,6,6-tetramethyl-4-piperidone in batch mode. For each test, an amount of 40 g (4 g/g) of the catalyst has been used. The temperature has been set to 65° C. Each test was run for 6 h, whereby ammonia was dosed over one hour before starting heating. The reaction product was analyzed with gas chromatography in order to determine its contents of 2,2,6,6-tetramethyl-4-piperidone, 2,2,4,6-tetramethyl-2,3-dihydropyridine, 1,2,5,6-tetrahydro-2,2,4,6,6-pentamethylpyrimidine, and acetone. Thus, the results according to the gas chromatographic measurements are given in area-%.

As can be gathered from the results shown in table 3, catalysts 1 and 4 comprising a zeolitic material having an SAR of 25 and 20, respectively shows a higher conversion towards 2,2,6,6-tetramethyl-4-piperidone than comparative catalyst 3 comprising a zeolitic material having an SAR of 5.2. In particular, the relative amount of 2,2,6,6-tetramethyl-4-piperidone is higher for catalysts 1 and 4 than comparative catalyst 3 over the whole testing time of 6 hours.

Further, as it can be seen in table 3, the relative amount as determined with gas chromatography of the undesired by-product 2,2,4,6-tetramethyl-2,3-dihydropyridine for both catalyst 1 and 4, and Comparative catalyst 3 has a comparatively low level. In sum, it can be seen from table 3 that catalysts 1 and 4 are more active catalysts in particular as regards the conversion to 2,2,6,6-tetramethyl-4-piperidone.

As can be gathered from the results shown in table 3, catalyst 1 and 4 shows superior catalytic performance compared to all comparative catalysts 1, and 3-6. In particular, the relative amount of 2,2,6,6-tetramethyl-4-piperidone is significantly higher for catalyst 1 and 4, whereby the relative amount of the undesired by-product 2,2,4,6-tetramethyl-2,3-dihydropyridine is significantly lower than for comparative catalyst 4 and comparable with comparative catalyst 1. It can be further seen in table 3 that the relative amount of 1,2,5,6-tetrahydro-2,2,4,6,6-pentamethyl-pyrimidine is significantly lower for catalyst 1 and 4, also the overall conversion of acetone is higher for catalyst 1 and 4 compared to all comparative catalysts 1, and 3-6.

Further, it can be seen in table 3 that the ratio of 2,2,6,6-tetramethyl-4-piperidone:2,2,4,6-tetramethyl-2,3-dihydropyridine is significantly higher for catalyst 1 and 4 compared to comparative catalysts 1, and 3-6.

In addition to that, it can be gathered from table 3 that comparative catalyst 6 comprising a zeolitic material having an MFI framework structure and having a silica-to-alumina molar ratio (SAR) of 30 shows an overall inferior performance compared to catalyst 1 and 4.

TABLE 3

Results for catalytic testing of different zeolites in batch mode, where the conversion towards a respective compound is given in area-% as determined by GC

| Catalyst | SAR | 2,2,6,6-tetramethyl-4-piperidone | 2,2,4,6-tetramethyl-2,3-dihydropyridine | 1,2,5,6-tetrahydro-2,2,4,6,6-pentamethyl-pyrimidine | Acetone | 2,2,6,6-tetramethyl-4-piperidone:2,2,4,6-tetramethyl-2,3-dihydropyridine |
|---|---|---|---|---|---|---|
| 1 | 25 | 19.04 | 1.36 | 0.49 | 74.05 | 14.00 |
| 4 | 20 | 20.28 | 1.70 | 0.97 | 71.75 | 11.92 |
| Comp. 1 | 6 | 13.61 | 1.54 | 2.35 | 76.15 | 8.84 |
| Comp. 3 | 5.2 | 4.46 | 0.88 | 4.85 | 86.97 | 5.07 |
| Comp. 4 | 10 | 3.22 | 1.91 | 4.80 | 84.63 | 1.69 |
| Comp. 5 | 15 | 0.82 | 0.29 | 9.45 | 86.25 | 2.83 |
| Comp. 6 | 30 | 0.65 | 0.34 | 9.44 | 86.21 | 1.91 |

The characteristic features for the tested zeolitic materials are listed in tables 1 and 2 above.

Example 2: Catalytic Testing—Continuous Mode

Catalyst 2 and comparative catalyst 2 have been tested as catalyst for the production of 2,2,6,6-tetramethyl-4-piperidone in continuous mode. A reactor with 1 m length and 8 mm diameter has been used. The temperature of the reactor wall was set to 70° C., the liquid hourly space velocity to 1.71 ml/g h, and the pressure to about 55 bar (single phase). The feed stream contained acetone and ammonia in a molar ratio of 14.3:1.0. Each test was run for 6 h. The average residence time has been found to be about 60 to 74 min.

For the catalyst testing in the continuous mode, the respective catalysts were employed as shaped bodies. To this effect, 1250 g of the respective zeolitic material, 1180 ml deionized water and 62.5 g Walocel™ (Walocel MW 15000 GB, Wolff Cellulosics GmbH & Co. KG, Germany) were provided in a kneader and kneaded for 10 minutes. For shaping, the kneaded mass was extruded at a pressure of 190 bar(abs) to give strands with a circular cross-section having a diameter of 1.5 mm. The strands were then dried at 120° C. for 12 h and calcined at 500° C. for 5 h. The reaction product was analyzed with gas chromatography in order to determine its contents of 2,2,6,6-tetramethyl-4-piperidone, 2,2,4,6-tetramethyl-2,3-dihydropyridine, 1,2,5,6-tetrahydro-2,2,4,6,6-pentamethyl-pyrimidine, and acetone. Thus, the results according to the gas chromatographic measurements are given in area-%.

As can be gathered from the results shown in table 4, catalyst 2 shows a higher conversion to 2,2,6,6-tetramethyl-4-piperidone also in continuous mode compared to comparative catalyst 2. As can be seen in table 4, the ratio 2,2,6,6-tetramethyl-4-piperidone:2,2,4,6-tetramethyl-2,3-dihydropyridine is higher for catalyst 2 than for comparative catalyst 2. This finding is all the more surprising since prior art Cavani et al., as discussed above, suggest using in particular a H-Y zeolite having a comparatively low SAR of 6 since it showed the best results as regards preparation of desired 2,2,6,6-tetramethyl-4-piperidone while producing a minimum of undesired by-product 2,2,4,6-tetramethyl-2,3-dihydropyridine. In comparison thereto, the H-Y zeolite having an SAR of tested by Cavani et al. in Journal of Molecular Catalysis A: Chemical 393 (2014), 325-332, showed a comparatively inferior performance as regards the preparation of 2,2,6,6-tetramethyl-4-piperidone as well as regards said by-product. Similarly, J. Tian et al. in Journal of Heterocyclic Chemistry 2015, vol. 52, p. 1377-1381, as discussed above, found that a H-Y zeolite having a silica-to-alumina molar ratio of 11.2 was the most effective for the preparation of 2,2,6,6-tetramethyl-4-piperidone. Obviously, J. Tian considered a zeolite having a comparatively low SAR as most promising as regards further experiments in particular as regards Acetone the optimization of the applied reaction conditions. In contrast thereto, and in particular considering a process mode allowing only a limited content of water according to the present invention, the inventive process comprising a zeolitic material having the FAU framework structure type surprisingly shows a technical effect also for zeolitic material having comparatively higher silica-to-alumina ratios.

The characteristic features for the tested zeolitic materials are listed in tables 1 and 2 above.

TABLE 4

Results for catalytic testing of different zeolites in continuous mode, where the conversion towards a respective compound is given in area-% as determined by GC

| Catalyst | SAR | 2,2,6,6-tetra-methyl-4-pi-peridone | 2,2,4,6-tetra-methyl-2,3-di-hydropyridine | 1,2,5,6-tetra-hydro-2,2,4,6,6-pentamethyl-pyrimidine | Acetone | 2,2,6,6-tetramethyl-4-piperidone:2,2,4,6-tetramethyl-2,3-dihydropyridine |
|---|---|---|---|---|---|---|
| 2 | 25 | 14.35 | 1.22 | 1.36 | 78.60 | 11.76 |
| Comp. 2 | 6 | 12.59 | 1.53 | 1.42 | 79.48 | 8.23 |

CITED LITERATURE

Figure 1:
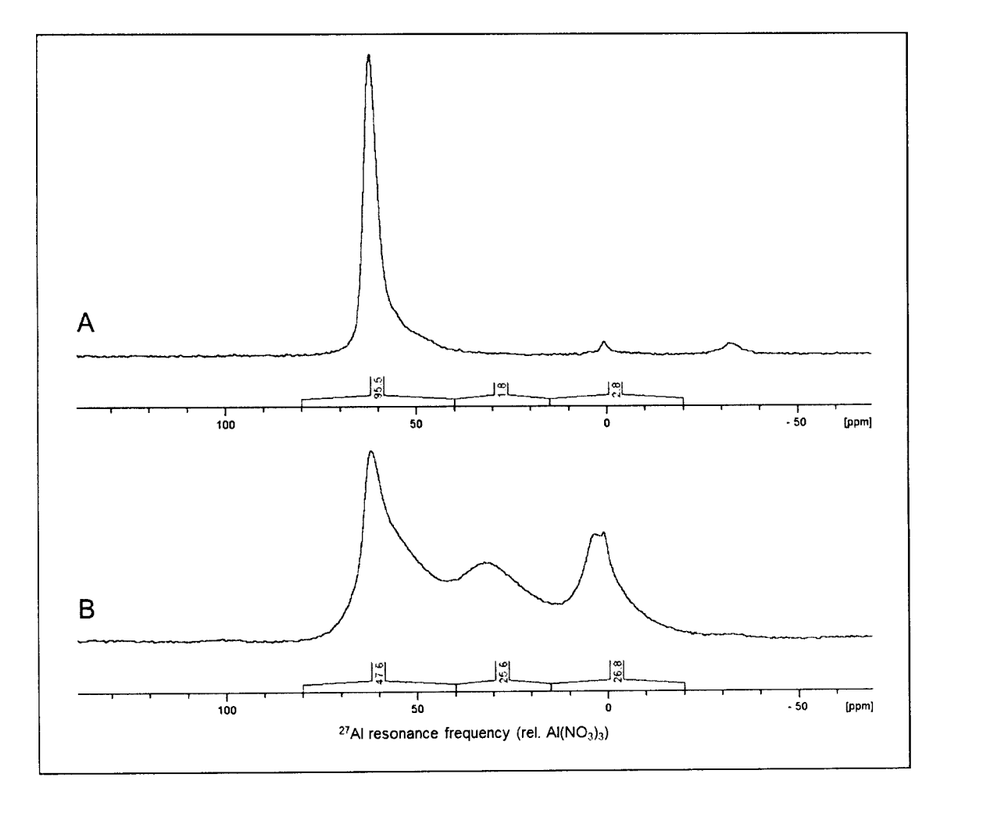
FIG. 1: shows the solid state $^{27}$Al NMR spectra of the zeolitic material according to Example 1 (top) relative to the zeolitic material of Comparative Example 1 (bottom), wherein the chemical shift in ppm is plotted along the abscissa and the relative intensity in arbitrary units is shown along the ordinate.

F. Cavani et al. in Journal of Molecular Catalysis A: Chemical 393 (2014), 325-332
CN 107033066 A
J. Tian et al. in Journal of Heterocyclic Chemistry 2015, vol. 52, p. 1377-1381

The invention claimed is:

1. A process for the production of 2,2,6,6-tetramethyl-4-piperidone comprising
 (i) providing a reactor containing a catalyst comprising a zeolitic material having a framework structure of FAU, wherein the zeolitic material comprises $YO_2$ and $X_2O_3$ in its framework structure, wherein Y is a tetravalent element and X is a trivalent element, wherein the zeolitic material has an $YO_2$ to $X_2O_3$ molar ratio of 16 to 175;
 (ii) preparing a reaction mixture comprising acetone and ammonia;
 (iii) contacting the catalyst in the reactor with the reaction mixture prepared in (ii) at a temperature in the range of from 40 to 250° C. for obtaining a reaction product comprising 2,2,6,6-tetramethyl-4-piperidone;
 wherein the mixture prepared in (ii) and contacted with the catalyst in (iii) contains less than 10 wt.-% of water based on 100 wt.-% of the reaction mixture.

2. The process of claim 1, wherein from 5 weight-% or more of the catalyst consist of the zeolitic material.

3. The process of claim 1, wherein the catalyst is provided as a powder and/or as a molding.

4. The process of claim 1, wherein Y is selected from the group consisting of Si, Sn, Ti, Zr, Ge, and mixtures of two or more thereof.

5. The process of claim 1, wherein X is selected from the group consisting of B, Al, Ga, In, Sc, Y, La, Ce, Pr, Nd, Pm, Sm, Eu, Gd, Tb, Dy, Ho, Er, Tm, Yb, Lu, and mixtures of two or more thereof.

6. The process of claim 1, wherein the zeolitic material is in the ammonium-form or in the H-form.

7. The process of claim 1, wherein the zeolitic material has a crystallinity in the range of from 50 to 100 weight-%, wherein the crystallinity is determined as described in Reference Example 3.

8. The process of claim 1, wherein $YO_2$, calculated as the element Y, is contained in the zeolitic material in the range of from 35.0 to 47.0 weight-%, based on the total weight of the zeolitic material.

9. The process of claim 1, wherein $X_2O_3$, calculated as X, is contained in the zeolitic material in the range of from 1.0 to 4.5 weight-%, based on the total weight of the zeolitic material.

10. The process of claim 1, wherein in (iii) the contacting of the catalyst with the reaction mixture prepared in (ii) is conducted at a temperature in the range of from 45 to 200° C.

11. The process of claim 1, wherein the process is conducted as a batch process or as a continuous process.

12. The process of claim 1, wherein in the reaction mixture prepared in (ii), the molar ratio of acetone to ammonia is in the range of from 5:1 to 25:1.

13. The process of claim 1, wherein the catalyst is provided as a molding, wherein the molding is prepared according to a process comprising (a) preparing a mixture comprising the zeolitic material and optionally one or more binders;
(b) shaping the mixture;
(c) optionally drying the shaped material in a gas atmosphere; and
(d) calcining the shaped material obtained from (b) or (c) in a gas atmosphere to obtain the molding.

* * * * *